United States Patent [19]

Magill

[11] Patent Number: 5,401,168
[45] Date of Patent: Mar. 28, 1995

[54] DRIVE TUBE APPARATUS

[75] Inventor: Thomas S. Magill, New Hope, Minn.

[73] Assignee: Universal Dynamics, Inc., Minneapolis, Minn.

[21] Appl. No.: 62,393

[22] Filed: May 17, 1993

[51] Int. Cl.⁶ .............................................. A61C 3/00
[52] U.S. Cl. ........................................ 433/18; 433/21
[58] Field of Search ............... 433/7, 18, 19, 20, 21, 433/22, 6

[56] References Cited

U.S. PATENT DOCUMENTS

| | | | |
|---|---|---|---|
| 597,582 | 1/1898 | Knapp | 433/7 |
| 787,861 | 4/1904 | Shelp | 433/18 |
| 1,202,798 | 10/1916 | Canning | 433/21 |
| 3,454,001 | 7/1969 | Stockfisch . | |
| 3,529,353 | 9/1970 | Schiaroli . | |
| 4,026,023 | 5/1977 | Fisher . | |
| 4,045,871 | 9/1977 | Nelson . | |
| 4,197,644 | 4/1980 | Ackerman, Jr. | 433/7 |
| 4,239,487 | 12/1980 | Murdock | 433/7 |
| 4,347,054 | 8/1982 | Kraus et al. | 433/7 |
| 4,431,411 | 2/1984 | Witzig et al. | 433/6 |
| 4,482,318 | 11/1984 | Forster | 433/7 |
| 4,483,674 | 11/1984 | Schütz | 433/22 |
| 4,573,914 | 3/1986 | Nord | 433/18 |

Primary Examiner—Gene Mancene
Assistant Examiner—Cindy A. Cherichetti
Attorney, Agent, or Firm—Leone & Moffa

[57] ABSTRACT

A drive tube apparatus for providing a precisely adjustable linear range of motion to orthodontic devices. The drive tube apparatus includes a threaded tube with a roughened surface for secure attachment to a mounting. A drive screw engages the threaded tube through a predetermined range of motion. A ball and socket rotatably attaches the drive screw to the drive shaft allowing the drive shaft to move within a linear range of motion without rotating with the drive screw. The drive shaft attached to and accomplishes the positioning of an adjustable appliance.

20 Claims, 5 Drawing Sheets

DRIVE TUBE APPARATUS

This invention relates to an orthodontic drive tube apparatus for precisely adjusting the position of a bite block, and more particularly to a orthodontic drive tube with a roughened surface for improved retention and a larger screw for ease of adjustment.

BACKGROUND OF THE INVENTION

Prior art drive tubes have been used in dental equipment to finely adjust the size, shape and positioning of orthodontic appliances. The prior art provides a number of devices for adjusting orthodontic appliances. Prior art devices include the Orthodontic Expansion Screw, U.S. Pat. No. 4,347,054, from Hans-Joachim Kraus and Berthold Walter, both of Germany. U.S. Pat. No. 4,347,054 discloses an adjustment device having two screw bodies displaceable through a screw spindle. The screw spindle has sections of counter rotating threads engaging threaded bores in opposed sections.

Prior art also provides an Orthodontic Spreader, U.S. Pat. No. 4,482,318, from Rolf Forster, also of Germany. The Orthodontic Spreader comprises an actuating screw for moving pressure transmitting nuts in opposite directions. Slideably mounted guide rods are mounted in both pressure transmitting nuts.

Some prior art adjustment devices are too large for some applications. Also, prior art drive tubes do not maintain solid contact with a bite block mounting and become unattached and move during adjustment. Prior art drive tubes have small diameter screw heads making adjustment difficult. Universal Dynamics, Inc. of Minneapolis, Minn. has been providing drive tubes for the orthodontic industry for a number of years, the latest improvements being part of the apparatus of the invention.

It is therefore the motive of the invention to provide a drive tube with a large diameter screw head facilitating adjustment with a roughened surface that provides a strong attachment to a bite block.

SUMMARY OF THE INVENTION

The invention provides a drive tube apparatus for providing a precisely adjustable linear range of motion to orthodontic devices. The drive tube apparatus includes a threaded tube with a roughened surface for secure attachment to a mounting. A drive screw engages the threaded tube through a predetermined range of motion. A ball and socket rotatably attaches the drive screw to the drive shaft allowing the drive shaft to move within a linear range of motion without rotating with the drive screw. The drive shaft attaches to and accomplishes the positioning of an adjustable appliance.

Other objects, features and advantages of the present invention will become apparent to those skilled in the art through the Description of the Preferred Embodiment, Claims, and Drawings herein wherein like numerals refer to like elements.

BRIEF DESCRIPTION OF THE DRAWINGS

To illustrate this invention, a preferred embodiment is described herein with reference to the accompanying drawings. The preferred embodiment concerns a drive tube apparatus.

DETAILED DESCRIPTION OF THE PREFERRED EMBODIMENT

Figure 1:
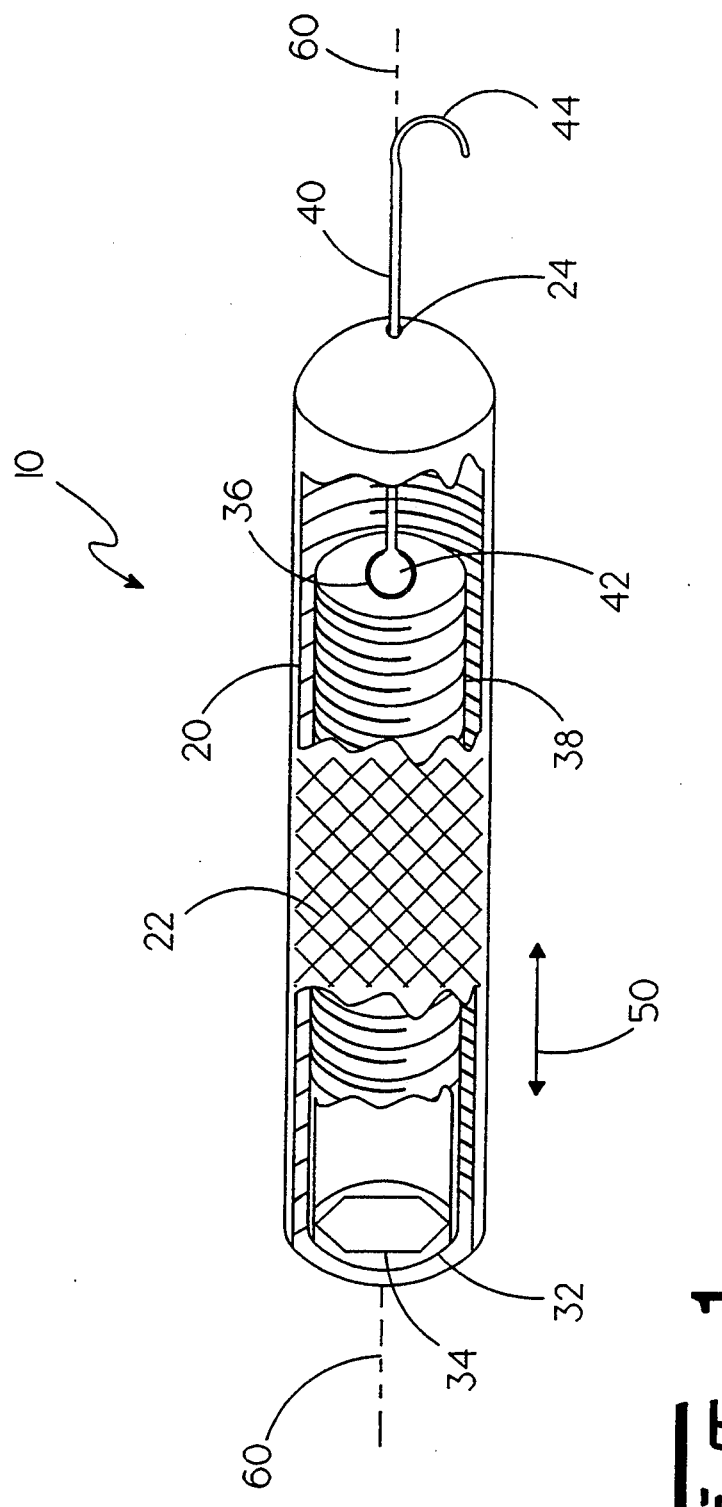
FIG. 1 schematically shows a three dimensional cutaway perspective view of a portion of the drive tube of the invention.

FIG. 1 schematically shows a three dimensional cutaway perspective view of a portion of the drive tube of the invention. The drive tube 10 has a threaded tube 20. Threaded tube 20 has 9 roughened outer surface 22. The roughened outer surface 22 provides for improved attachment between drive tube 10 and a mounting. The apparatus of the invention also has a drive screw 38. The drive screw 38 is suitably threaded to engage the threaded tube 20. In this example of the present invention the drive screw 38 also has a screw head 32 with a large diameter hexagonal aperture 34. The large diameter of hexagonal aperture 34 in screw head 32 enables easy adjustment of the drive screw 38. During adjustment, the drive screw 38 engages the threaded tube 20 and provides linear movement of the drive screw 38 along an axis 60 of the threaded tube 20.

The drive screw 38 also has a socket 36. The socket 36 is located on an internal end of the drive screw 38. The apparatus of the invention also has a drive shaft 40. The drive shaft 40 has a ball 42 on an internal end. The ball 42 of the drive shaft 40 is suitably sized to fit within the socket 36 of the drive screw 38 in a ball and socket arrangement. The ball 42 rotatably attaches the drive shaft 40 to the drive screw 38. The drive shaft 40 passes through an opening 24 in the threaded tube 20. The opening 24 in the threaded tube 20 allows the drive shaft 40 to slide along the axis 60 of the threaded tube 10 but restrains motion in other directions. The drive Shaft 40 has an external end forming a hook 44 which is adapted to be attached to a movable piece.

In one example embodiment of the invention, engagement of the drive screw 38 with an allen wrench in the hexagonal aperture 34 accomplishes an adjustment of the position of the drive shaft 40. When the drive screw 38 is rotated, motive force is provided to the drive screw 38 and drive shaft 40 in 10 one of the directions indicated by a double-headed arrow 50.

Figure 2B:
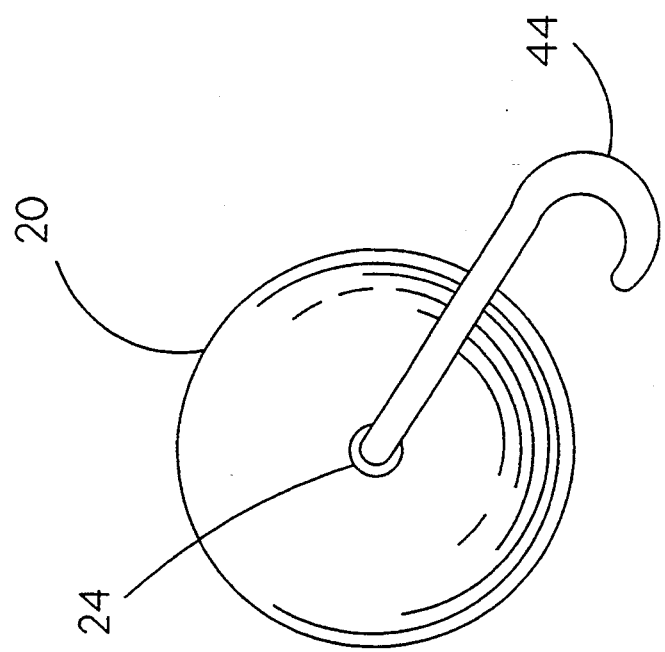
FIG. 2b schematically shows a rear view of the apparatus of the invention looking into the drive tube of the invention.
Figure 2A:
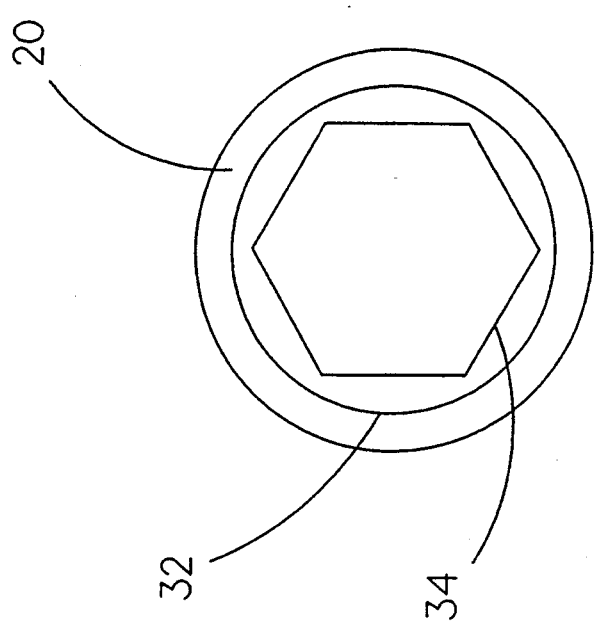
FIG. 2a schematically shows a front view of the apparatus of the invention looking into the drive tube of the invention.

FIG. 2a schematically shows a front view of the apparatus of the invention looking into the drive tube of the invention. This portion shows the drive tube 20. The drive screw 38 engages the threaded tube 20. The hexagonal aperture 34 is located on the screw head 32 of the drive screw 38. As indicated hereinabove, in one example embodiment of the invention, the drive screw 38 is manipulated by using an allen wrench in the hexagonal aperture 34.

FIG. 2b schematically shows a rear view of the apparatus of the invention looking into the drive tube 10 of the invention. This portion shows the opening 24 in the threaded tube 20. The drive shaft extends through the opening 24. The opening 24 allows the drive shaft 40 to move slideably along the axis of the threaded tube 20, but restrains motion in all other directions. The hook 44 forms one end of the drive shaft 40. As explained hereinabove, adjustment of the linear position of the drive shaft 40 is accomplished by the manipulation of the drive screw 38.

Figure 3:
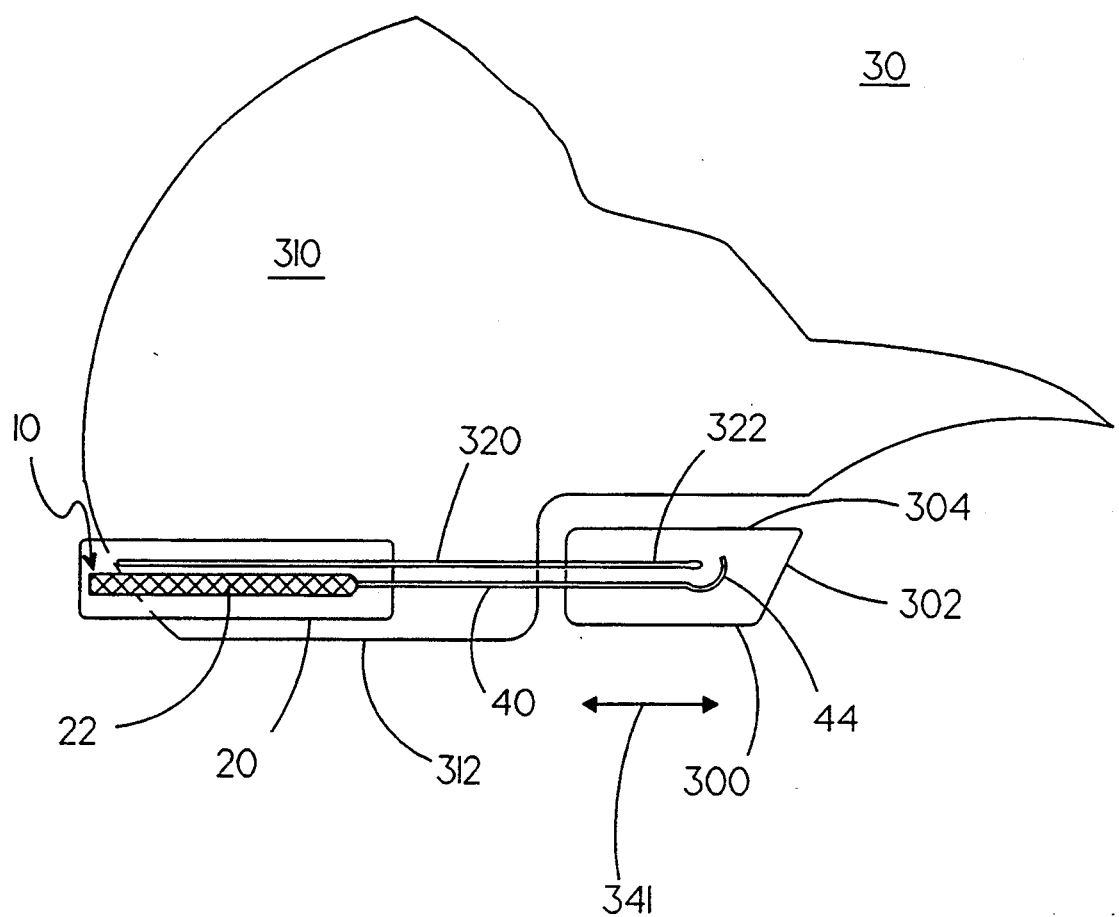
FIG. 3 shows a side view of one example embodiment of the drive tube of the invention as installed in an orthodontic appliance.

FIG. 3 shows a side view of one example embodiment of the drive tube of the invention as installed in an orthodontic appliance 30 in a partial cross sectional view. FIG. 3 demonstrates how the drive tube of the invention may be advantageously used to provide adjustment capabilities to an orthodontic appliance 30. The orthodontic appliance 30 has an upper palate plate 310, worn within the mouth of the patient and attached by conventional wire retaining means to the upper teeth. The shown section of palate plate 310 comprises an integrated, molded palate plate bite block 312. The molded palate plate bite block 312 may be advantageously fashioned so as to rest over the occlusal surface of the maxillary first molar. The shown section of the orthodontic appliance 30 also has an adjustable bite block 300, with an angled pressure surface 302.

A stainless steel wire connector 320 attaches the adjustable bite block 300 to the molded palate plate bite block 312. The stainless steel wire connector 320 slideably attaches the adjustable bite block 300 to the molded palate plate bite block 312. The stainless steel wire connector 320 may advantageously be fashioned in the form of a U-shaped loop 322. The U-shaped loop 322 may be advantageously anchored within the adjustable bite block 300. The two ends of the stainless steel wire connector 320 may advantageously pass from the adjustable bite block 300 into the molded palate plate bite block 312 in a generally parallel fashion. The parallel ends of the stainless steel wire connector 320 serve as guide rods and slide laterally within the molded palate plate bite block 312 while restricting motion of the adjustable bite block 300 in any other direction.

The drive shaft 40 provides the means of extending and retracting the adjustable bite block 300 in cooperation with a drive tube 10 where the drive tube 10 is fashioned in accordance with the principles of the invention as described hereinabove. The drive tube 10 includes a threaded tube 20. One end of the drive shaft 40 may advantageously form a hooked end 44 which anchors the drive shaft 40 within the adjustable bite block 300. The hooked end 44 may advantageously pass over and around the U-shaped loop 322 of the stainless steel wire connector 320. The other end of the drive shaft 40 passes into the drive tube 10 and attaches to the drive screw (not shown). The stainless steel wire connector 320 serves as a guide for adjustment of the adjustable bite block 300.

The drive tube 10 may advantageously be embedded within the molded palate plate bite block 312 of palate plate 310. The roughened surface 22 of the threaded tube 20 maintains a stable attachment within the palate plate bite block 312. Manipulating the drive tube 10 provides motive force in the directions indicated by a double-headed arrow 341. The drive shaft 40 is moved laterally by rotational manipulation of the drive screw 38 (shown in FIG. 4). The stable contact provided by roughened surface 22 maintains the relative position of the drive tube 10. In this way, movement of the drive shaft 40 provides for the extension and retraction of the attached adjustable bite block 300. The positioning of the adjustable bite block 300 is thus accomplished through adjustment of the drive tube 10.

The adjustable bite block 300 also has an upper pressure surface 304. When the adjustable bite block 300 is inserted into the mouth of the patient, the upper pressure surface 304 rests on the occlusal surface of the upper buccal teeth, providing support for the adjustable bite block 300 in the vertical plane of the mouth.

The angled pressure surface 302 slopes downward and towards the rear of the mouth. The angled pressure surface 302 acts in cooperation with an opposing angled surface of a lower bite block, similar to surface 18 shown in FIG. 1, during a biting motion. The biting motion produces a forward mandibular displacement that operates to correct Class 2 malocclusions.

FIG. 3 shows how the drive tube 10 provides an adjustment means that is used to position the angled pressure surface 302 for increased effectiveness through the progression of treatment. Other applications of the drive tube 10 are possible, as will be recognized by those skilled in the art having the benefit of this disclosure.

Figure 4:
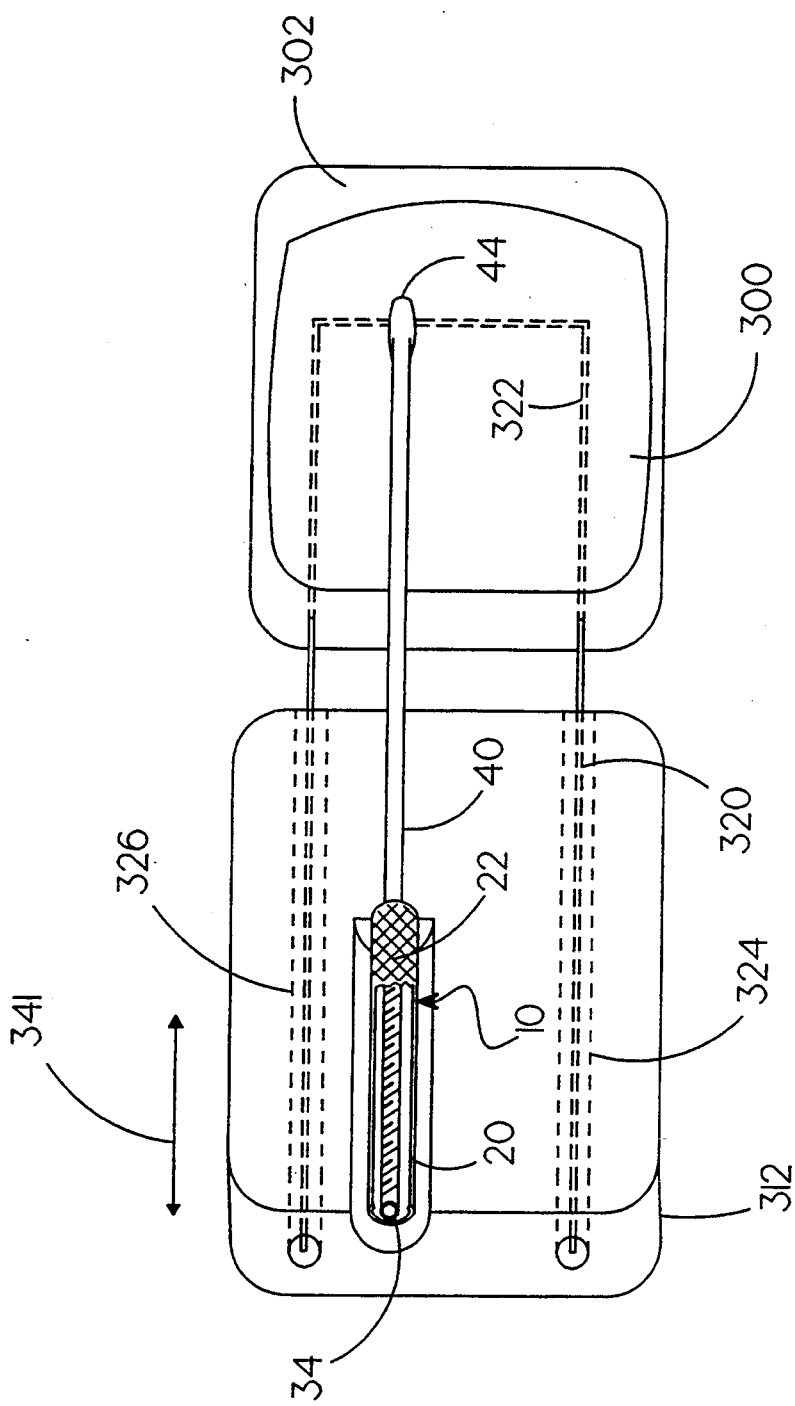
FIG. 4 shows a top view in cross section of one example embodiment of the drive tube of the invention as employed in an orthodontic appliance.

FIG. 4 shows a top view in cross section of one example embodiment of the drive tube of the invention. This portion shows the application of the drive tube of the invention in an orthodontic appliance which comprises the drive tube apparatus 10, the molded palate plate bite block 312, the adjustable bite block 300, and the angled pressure surface 302.

FIG. 4 shows in greater detail the application of the drive tube of the invention in adjusting the position of the adjustable bite block 300. The stainless steel wire connector 320 provides a means of slideably attaching the adjustable bite block 300 to the molded palate plate bite block 312. The stainless steel wire collector 320 has the J-shaped loop 322 embedded within the adjustable bite block 300, and two ends passing into the molded palate plate bite block 312. The two ends of the stainless steel wire connector 320 slide within a pair of cylinders 324 and 326 that are molded into the molded palate plate bite block 312 so as to allow adjustment of the adjustable bite block 300. The drive tube 10 is embedded within the molded palate plate bite block 312. The roughened surface 22 of the threaded tube 20 maintains a secure attachment within the molded palate plate bite block 312. The drive shaft 40 extends from the threaded tube 20 and provides a means of extending and retracting the adjustable bite block 300. The hooked end 44 formed by the drive shaft 40 may be advantageously embedded in the adjustable bite block 300. The hooked end 44 passes over and partially around the U-shaped loop 322 of stainless steel wire connector 320, anchoring the position of the drive shaft 40 within the bite block 300. Rotational manipulation of the drive tube 10 provides motive force for the adjustable bite block 300 in the directions indicated by the doubleheaded arrow 341.

In one embodiment of the invention, the position of the adjustable bite block 300 may be adjusted by inserting an allen wrench into aperture 34 and rotating the drive screw 38. Rotation of the drive screw 38 is translated into lateral movement by the threaded end 334, extending and retracting the drive shaft 40, depending upon the rotational direction of the drive tube. The stainless steel wire connector 320 acts as a guide rod and prevents rotation of the drive shaft 40 while allowing the adjustable bite block 300 to be extended and retracted by drive shaft 40.

Figure 5:
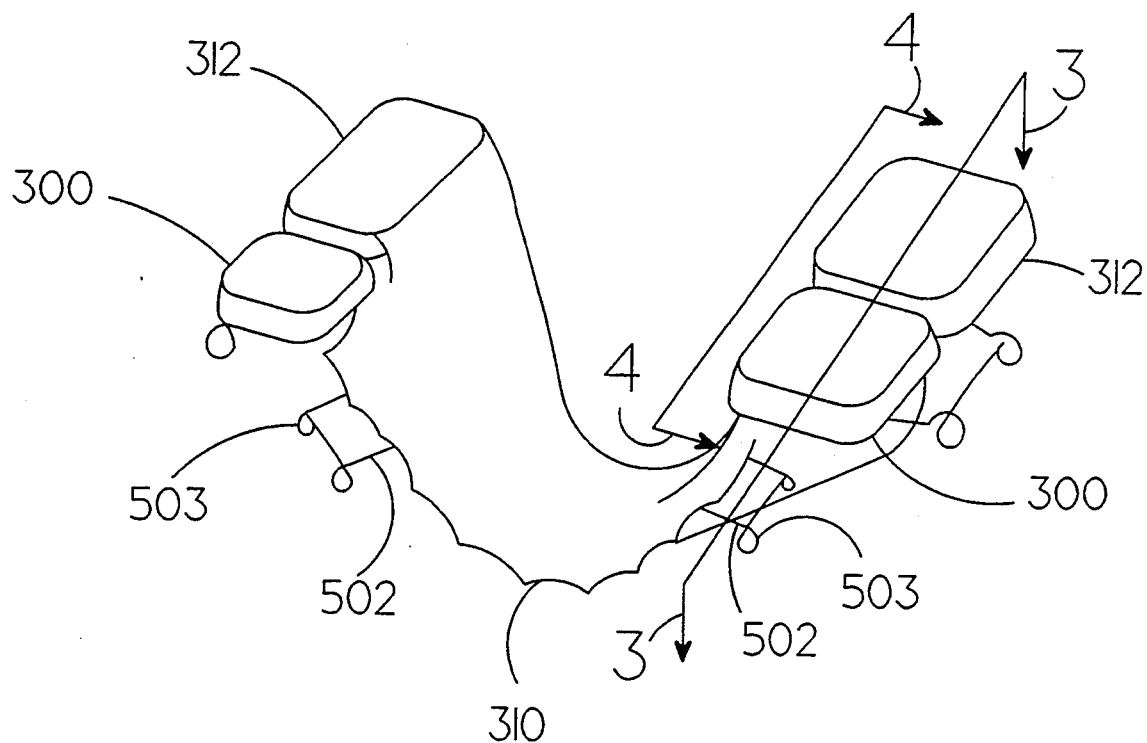
FIG. 5 shows a three dimensional perspective of one example embodiment of an orthodontic appliance of the drive tube of the invention.

FIG. 5 shows a three dimensional perspective of one example embodiment of an orthodontic appliance which may apply the drive tube of the invention. Arrows 3—3 show the cutaway perspective shown by FIG. 3. Arrows 4—4 shows the cutaway perspective shown by FIG. 4.

The invention has been described herein in considerable detail in order to comply with the Patent Statutes and to provide those skilled in the art with the information needed to apply the novel principles and to construct and use such specialized components as are required. How ever, it is to be understood that the invention may be carried out by specifically different equipment and devices and that various modifications, both as to the equipment details and operating procedures, may be accomplished without departing from the scope of the invention itself.

What is claimed

1. A drive tube apparatus for installation within an orthodontic appliance for treating skeletally based dental malocclusions, the orthodontic appliance having a mount, the drive tube apparatus comprising:
   (a) a drive screw having an adjustment end and a drive end;
   (b) threaded tube means for receiving the drive screw, wherein the threaded tube means is positioned within the mount, wherein the threaded tube means further includes an outer surface, the outer surface having a means for retaining the threaded tube means within the mount; and drive shaft means for driving the orthodontic appliance connected to the
   (c) drive end, wherein the means for retaining the threaded tube means within the mount comprises a roughened surface on the threaded tube means.

2. The drive tube apparatus of claim 1 wherein the threaded tube means has a longitudinal axis and the drive shaft means is supported at one end of the threaded tube means so that the drive shaft means slides linearly along the longitudinal axis when the drive screw is actuated.

3. The drive tube apparatus of claim 1 wherein the adjustment end of the drive screw comprises a screw head having a large diameter aperture suitable for accepting an external adjustment tool.

4. The drive tube apparatus of claim 1 wherein the drive end further includes a socket.

5. The drive tube apparatus of claim 4 wherein a first end of the drive shaft means comprises a ball means adapted to cooperate with the socket to attach the drive shaft means to the drive screw means.

6. The drive tube apparatus of claim 5 wherein a second end of the drive shaft means forms a hook extending from the threaded tube means.

7. A drive tube apparatus for adjusting a movable bite block relative to an orthodontic mount, the drive tube apparatus comprising:
   (a) a cylindrical housing having a roughened outer surface and an opening on a first end of the cylindrical housing;
   (b) a drive screw having a threaded portion engaging the cylindrical housing wherein the drive screw includes an exposed end having a screw head having a large face with a hexagonal aperture, the drive screw also having an internal end forming a socket; and
   (c) a drive shaft it extending from the cylindrical housing through the opening of the cylindrical housing and linearly along a longitudinal axis of the drive tube, wherein a first end of the drive shaft comprises a ball cooperating with the socket to connect to the drive screw and a second end comprises a hook positioned to attach to the movable bite block.

8. An orthodontic apparatus for treating skeletally based dental malocclusions, the orthodontic apparatus comprising:
   (a) upper palate plate means having an adjustable block mount;
   (b) lower palate plate means having a lower bite block, wherein the lower bite block has a first surface; and
   (c) adjustment means, affixed to the upper palate plate means, for positioning a moveable bite block, the moveable bite block having a second surface, the second surface being positioned and arranged to contact the first surface so as to provide a malocclusion correction force wherein the adjustment means comprises a drive tube apparatus comprising:
      (1) a drive screw having an adjustment end and a drive end;
      (2) threaded tube means for receiving the drive screw, wherein the threaded tube means is positioned within the upper palate plate means, wherein the threaded tube means further includes an outer surface, the outer surface having a means for retaining the threaded tube means within the upper palate plate means; and
      (3) drive shaft means for driving the orthodontic appliance connected to the drive end.

9. The orthodontic apparatus of claim 8 wherein the threaded tube means has a longitudinal axis and the drive shaft means is supported at one end of the threaded tube means so that the drive shaft means slides linearly along the longitudinal axis When the drive screw is actuated.

10. The drive tube apparatus of claim 9 wherein the adjustment end of the drive screw comprises a screw head having a large diameter aperture suitable for accepting an external adjustment tool.

11. The drive tube apparatus of claim 8 wherein the drive end further includes a socket.

12. The drive tube apparatus of claim 11 wherein a first end of the drive shaft means comprises a ball means adapted to cooperate with the socket to attach the drive shaft means to the drive screw.

13. The drive tube apparatus of claim 12 wherein a second end of the drive shaft means forms a hook extending from the threaded tube means.

14. A drive tube apparatus for installation within an orthodontic appliance for treating skeletally based dental malocclusions, the orthodontic appliance having a mount, the drive tube apparatus comprising:
   (a) a drive screw having an adjustment end with a large access port for manual manipulation and a drive end;
   (b) threaded tube means for receiving the drive screw, wherein the threaded tube means is installed in the mount, wherein the threaded tube means has an outer surface, and the outer surface includes a means for retaining the threaded tube means within the mount; and
   (c) drive shaft means for driving the orthodontic appliance connected to the drive end, wherein the means for retaining the threaded tube means within the mount comprises a roughened surface on the threaded tube means.

15. The drive tube apparatus of claim 14 wherein the threaded tube means has a longitudinal axis and the drive shaft means is supported at one end of the threaded tube means so that the drive shaft means slides linearly along the longitudinal axis when the drive screw is actuated.

16. The drive tube apparatus of claim 1 wherein the adjustment end of the drive screw comprises a screw head having a large diameter aperture suitable for accepting an external adjustment tool.

17. The drive tube apparatus of claim 14 wherein the drive end further includes a socket.

18. The drive tube apparatus of claim 17 wherein a first end of the drive shaft means comprises a ball means adapted to cooperate with the socket to attach the drive shaft means to the drive screw.

19. The drive tube apparatus of claim 18 wherein a second end of the drive shaft means forms a hook extending from the threaded tube means.

20. A drive tube apparatus for installation within a orthodontic appliance having a mount, the drive tube apparatus comprising:
 (a) a threaded tube means installed on the mount, the threaded tube means having a means for retaining the threaded tube means within the mount further comprising a knurled outer surface;
 (b) a drive screw located within the threaded tube means having an adjustment end and a drive end; and
 (c) a drive shaft means for driving the orthodontic appliance connected to the drive end.

* * * * *

UNITED STATES PATENT AND TRADEMARK OFFICE
CERTIFICATE OF CORRECTION

PATENT NO. : 5,401,168
DATED : March 28, 1995
INVENTOR(S) : Thomas S. Magill

It is certified that error appears in the above-identified patent and that said Letters Patent is hereby corrected as shown below:

Column 2, line 22, delete number "9" and replace it with -- a --.

Column 2, line 28, after the word "tion" insert a -- , --.

Column 2, line 54, delete number "10".

Column 4, line 36 delete the letter "J" and replace it with -- U --.

Column 4, line 56, delete the word "doublesheaded" and replace it with -- double-headed --.

Column 5, line 12, delete the phrase "How ever" and replace it with -- However --.

In the Claims

Column 5, line 67, delete the word "it".

Column 6, line 38, delete the word "When" and replace it with -- when --.

UNITED STATES PATENT AND TRADEMARK OFFICE
CERTIFICATE OF CORRECTION

PATENT NO. : 5,401,168
DATED      : March 28, 1995
INVENTOR(S): Thomas S. Magill It is certified that error appears in the above-indentified patent and that said Letters Patent is hereby corrected as shown below:

Column 7, line 10, delete number "1" and replace it with --14--.

Signed and Sealed this

Sixteenth Day of April, 1996

Attest:

BRUCE LEHMAN

Attesting Officer     Commissioner of Patents and Trademarks